United States Patent
Wang et al.

(10) Patent No.: US 6,486,158 B1
(45) Date of Patent: Nov. 26, 2002

(54) [4,5]-FUSED-3,6-DISUBSTITUTED-PYRIDAZINES WITH SULFUR-CONTAINING SUBSTITUENTS IN POSITION THREE FOR THE TREATMENT OF NEOPLASIA

(75) Inventors: Xiaojing Wang, Livermore, CA (US); Gerhard Sperl, Horsham, PA (US); Paul Gross, Stockton, CA (US); Rifat Pamukcu, Spring House, PA (US); Gary A. Piazza, Doylestown, PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/875,107

(22) Filed: Jun. 6, 2001

Related U.S. Application Data

(63) Continuation of application No. 09/134,346, filed on Aug. 14, 1998, now abandoned.

(51) Int. Cl.[7] .................. C07D 471/04; C07D 237/32; A61K 31/502; A61K 31/5025; A61P 35/00
(52) U.S. Cl. .................. 514/248; 544/105; 544/184; 544/180; 544/235; 544/236; 544/237
(58) Field of Search .................. 544/236; 514/248

(56) References Cited

U.S. PATENT DOCUMENTS 4,223,142 A * 9/1980 Denzel .................. 544/236

OTHER PUBLICATIONS

Hajek, Neoplasma 43, 141 (1996).*

* cited by examiner

*Primary Examiner*—Mark L. Berch

(74) *Attorney, Agent, or Firm*—Robert W. Stevenson

(57) ABSTRACT

[4,5]-Fused-3,6 disubstituted-pydidazines of Formula I are useful for inducing or promoting apoptosis and for arresting uncontrolled neoplastic cell proliferation, and are specifically useful in the arresting and treatment of neoplasia:

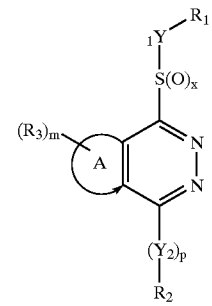

wherein $Y_1$ and $Y_2$ are independently selected from the group consisting of $(CH_2)_n$, —C(X)—NH—, —$(CH_2)_n$—C(X)—O—, and X is O or S;

$R_1$ is selected from the group consisting of lower alkyl, lower alkenyl, lower alkynyl, and substituted or unsubstituted phenyl, pyridinyl, and the like;

$R_2$ is selected from the group consisting of substituted or unsubstituted phenyl, benzyl, pyridinyl, and the like;

"A" is a benzene ring fused with the pyridazine ring; and $R_3$ is independently selected in each instance form the group consisting of halogen, lower alkyl, and the like.

33 Claims, No Drawings

[4,5]-FUSED-3,6-DISUBSTITUTED-PYRIDAZINES WITH SULFUR-CONTAINING SUBSTITUENTS IN POSITION THREE FOR THE TREATMENT OF NEOPLASIA

This application is a Continuation of prior U.S. application Ser. No. 09/134,346 filed Aug. 14, 1998 abandoned, entitled "[4,5]-Fused-3,6-Disubstituted-Pyridazines with Sulfur-Containing Substituents in Position Three for the Treatment of Neoplasia" which is incorporated herein by reference.

TECHNICAL FIELD

This invention relates to compounds and methods for inducing or promoting apoptosis and for arresting uncontrolled neoplastic cell proliferation, methods that are specifically useful in the arresting and treatment of neoplasias, including precancerous and cancerous lesions.

BACKGROUND OF THE INVENTION

Pharmaceuticals that are effective against early stage neoplasias comprise an emerging and expanding area of research and potential commercial development. Such pharmaceuticals can delay or arrest development of precancerous lesions into cancers. Each year in the United States alone, untold numbers of people develop precancerous lesions, which exhibit a strong statistically significant tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), cervical dysplasia (cervical cancer) and other such neoplasms.

Such compounds and methods are particularly beneficial to sub-populations of patients who repeatedly develop precancerous lesions, and therefore have a statistically higher probability of getting cancer. Many cancer types (e.g., breast, colon, prostate etc.) have such patient sub-populations.

The search for drugs useful for treating and preventing neoplasias in their earliest stages is intensive because chemotherapy and surgery on cancer itself is often not effective, and current cancer chemotherapy has severe side effects. Such cancer-preventative compounds are also envisaged for recovered cancer patients who retain a risk of cancer reoccurrence, and even for cancer patients who would benefit from compounds that selectively induce apoptosis in neoplastic, but substantially not in normal cells.

Because it is believed that chronic administration of cancer-preventative pharmaceuticals is necessary to inhibit or arrest the development of neoplasia, standard cancer chemotherapeutic drugs are not considered appropriate drugs for cancer chemoprevention because, whatever cancer preventative (as opposed to cancer-fighting) capabilities those drugs may possess, they do not outweigh their severe side effects. Most standard chemotherapeutics are now believed to kill cancer cells by inducing apoptosis (also sometimes referred to as "programmed cell death"). Apoptosis naturally occurs in many tissues in the body. Apoptosis plays a critical role in tissue homeostasis, that is, it ensures that the number of new cells produced are correspondingly offset by an equal number of cells that die. Apoptosis is especially pronounced in self-renewing tissues such as bone marrow, immune cells, gut, and skin. For example, the cells in the intestinal lining divide so rapidly that the body must eliminate cells after only three days to protect and prevent the overgrowth of the intestinal lining.

Standard chemotherapeutics promote apoptosis not only in cancer cells, but also in normal human tissues, and therefore have a particularly severe effect on tissues where apoptosis is especially pronounced (e.g. hair, gut and skin). The results of those effects include hair loss, weight loss, vomiting and bone marrow immune suppression. Thus, standard chemotherapeutics are inappropriate for cancer prevention, particularly if chronic administration is indicated.

Several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the continued prophylactic use of currently available NSAIDs, even in high colon cancer-risk patients, is still marked by severe side reactions that include gastrointestinal irritations, perforations, ulcerations and kidney toxicity believed to be produced by inhibition of prostaglandin synthetase activity ("PGE-2"). Such inhibition is a requirement for the NSAIDs anti-inflammatory action since elevated levels of PGE-2 are associated with inflammation. PGE-2 plays a protective function in the gastrointestinal tract, which is the reason such gastric side effects arise with chronic NSAID therapy, which is rarely indicated for arthritis sufferers, acute therapy being the norm for them. However, chronic administration of sulindac is important for high cancer-risk patients to eliminate and prevent future polyps which cause gastric side effects in many such patients. Once NSAID treatment is terminated due to such complications, the neoplasms return, particularly in high risk patients.

Compounds such as those disclosed in U.S. Pat. No. 5,643,959 have exhibited advantages in the treatment of neoplastic lesions since such compounds have been shown to induce apoptosis in neoplastic cells but not in normal cells in humans (see Piazza et al. Gastroenterology Vol. 112, A629, 1997). Thus, the severe side effects due to induction of apoptosis in normal cells by conventional chemotherapeutics are avoided by these novel therapeutics (see, Piazza et al. Cancer Research Vol. 57, pp. 2452–2459, 1997). In addition, such compounds do not exhibit the gastric side effects associated with NSAIDs since such compounds do not substantially inhibit PGE-2. More potent compounds with such neoplasia specificity but without substantial PGE-2 activity are desirable.

SUMMARY OF THE INVENTION

This invention represents potent compounds that inhibit the growth of neoplastic cells, for treating patients with neoplastic lesions without substantially inhibiting PGE-2. This invention also involves methods for inducing such specific inhibition of neoplastic cells by exposing such cells to a pharmacologically effective amount of those compounds described below to a patient in need of such treatment. Such compositions are effective in modulating the growth of neoplasms.

DETAILED DESCRIPTION OF THE INVENTION

As discussed above, the present invention includes compounds of Formula I below (as well as their pharmaceutically acceptable salts) for treating a patient with neoplastic, particularly precancerous, and cancerous lesions:

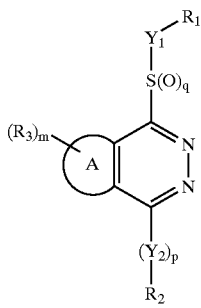

wherein
- $Y_1$ and $Y_2$ are independently selected from the group consisting of $(CH_2)_n$, $-C(X)-NH-$, $-(CH_2)_n-C(X)-O-$, $-C(X)-O-$ and X is O or S;
- $R_1$ is selected from the group consisting of lower alkyl, lower alkenyl, lower alkynyl, hydrogen, and substituted or unsubstituted phenyl, pyridinyl, pyrrolyl, pyrrolidinyl, pyrazolyl, pyrazolidinyl, imidazolyl, imidazolidinyl, piperidinyl, pyrazinyl, piperazinyl, pyzimidinyl, naphthyl, morpholinyl, tetrazolyl, triazinyl, furfulyl and thiophenyl, wherein said substituents are one to three independently selected from the group consisting of halogen, lower alkyl, lower alkoxy, amino, lower alkylamino, di-lower alkylamio, hydroxy, nitro, nitrile, carboxyl, sulfonylamido, lower alkyl mercapto, and lower alkyl sulfonyl;
- $R_2$ is selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, tetrazolyl, morpholinyl, triazinyl, furfuryl and thiophenyl, wherein said substituents are one to three independently selected from the group consisting of halogen, lower alkyl, lower alkoxy, amino, lower alkylanmino, di-lower alkylamino, hydroxy, nitro, nitrile, carboxyl, aminosulfonyl, lower alkyl mercapto, and lower alkyl;
- A is a ring fused with the pyridazine ring selected from the group consisting of benzene, pyndine, pyrrol, pyrtolidine, pyrazol, pyrazolidine, imidazol, imidazolidine, piperidine, pyrazine, piperazine, pyrimidine, morpholine, tetrazol, triazine, furan and thiophene; piperidine, pyrazine, piperazine, pyrimidine, morpholine, tetrazol, triazine, furan and thiophene;
- $(R_3)$ are substituents replacing hydrogen on the ring fused to pyridazine. $R_3$ is independently selected in each instance from the group consisting of halogen, lower alkyl, lower alkoxy, amino, lower alkylamino, di-lower alkylamino, hydroxy, nitro, nitrile, carboxyl, sulfonylamido, lower alkyl mercapto, and lower alkyl sulfonyl;
- m is an integer from 1 to 4;
- n is an integer from 0 to 3
- p is 0 or 1;
- q is 0, 1 or 2; and pharmaceutically acceptable salts thereof.

Preferred compounds of this invention include those where (1) $R_1$ is selected from the group consisting of lower alkyl, lower alkenyl, lower alkynyl, and substituted or unsubstituted phenyl, pyridinyl, pyrrolyl, pyrazolyl, imidazolyl, pyrazinyl, pyrimidinyl, morpholinyl, triazinyl, furfuryl and thiophenyl, wherein said substituents are one or two independently selected from the group consisting of halogen, lower alkoxy, di-lower alkylamino, hydroxy, nitrile, carboxyl, sulfonylamido, lower alkyl mercapto, and lower alkyl sulfonyl; (2) $R_2$ is selected from the group consisting of substituted or unsubstituted phenyl, benzyl, pyridinyl, pyrrolyl, pyrazolyl, imidazolyl, pyrazinyl, pyrimidinyl, morpholinyl, triazinyl, furfuryl and thiophenyl, wherein said substituents are one or two independently selected from the group consisting of halogen, lower alkyl, lower alkoxy, di-lower alkylamino, hydroxy, carboxyl, aminosulfonyl, lower alkyl mercapto, and lower alkyl; (3) "A" is a ring fused with the pyridazine ring selected from the group consisting of benzene, pyridine, pyrrol, pyrrolidine, imidazolidine, piperidine, pyrazine, piperazine, pyrimidine, morpholine, triazine, furan and thiophene; (4) p is 0 or 1; (5) $R_3$ is independently selected in each instance from the group consisting of halogen, lower alkyl, lower alkoxy, di-lower alkylamino, hydroxy, carboxyl, sulfonylamido, lower alkyl mercapto, and lower alkyl sulfonyl; and m is an integer from 0 to 2; and (6) n is an integer from 0 to 2.

More preferred compounds of this invention include those wherein (1) $R_1$ is selected from the group consisting of substituted or unsubstituted phenyl, pyridinyl, pyrazinyl, pyrimidinyl, triazinyl, furfuryl and thiophenyl, wherein said substituent is one member selected from the group consisting of halogen, lower alkoxy, di-lower alkylamino, nitrile, sulfonylamido, and lower alkyl sulfonyl; (2) $R_2$ is selected from the group consisting of substituted or unsubstituted phenyl, benzyl, pyridinyl, pyrazinyl, pyrimidinyl, triazinyl, furfuryl and thiophenyl, wherein said substituent is one member selected from the group consisting of halogen, lower alkyl, lower alkoxy, di-lower alkylamino, aminosulfonyl, and lower alkyl mercapto; (3) wherein "A" is a ring fused with the pyridazine ring selected from the group consisting of benzene, pyrazine, pyrimidine, furan and thiophene; (4) p is 0; (5) $R_3$ is independently selected in each instance from the group consisting of halogen, lower alkyl, lower alkoxy, di-lower alkylamino, and lower alkyl mercapto; and m is 0 or 1; and (6) n is 0 or 1.

The present invention is also a method of treating individuals with neoplastic lesions by administering a pharmacologically effective amount of an enterically coated pharmaceutical composition that includes compounds of this invention.

Preferably, such compounds are administered without therapeutic amounts of an NSAID.

Also, the present invention is a method of inhibiting the growth of neoplastic cells by exposing the cells to an effective amount of compounds of Formula I As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "cancerous" refers to lesions that are malignant. Examples include malignant melanomas, breast cancer, prostate cancer and colon cancer.

As used herein, the term "neoplasm" refers to both precancerous and cancerous lesions and hyperplasia.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to $C_1$ to $C_8$ alkyl groups.

The term "lower alkoxy" refers to alkoxy groups having from 1 to 8 carbons, including straight, branched or cyclic arrangements.

The term "lower alkylmercapto" refers to a sulfide group that is substituted with a lower alkyl group; and the term "lower alkyl sulfonyl" refers to a sulfone group that is substituted with a lower alkyl group.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmetate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

It will be appreciated that certain compounds of Formula I can possess an asymmetric carbon atom and are thus capable of existing as enantiomers. Unless otherwise specified, this invention includes such enantiomers, including any racemates. The separate enantiomers may be synthesized from chiral starting materials, or the racemates can be resolved by conventional procedures that are well known in the art of chemistry such as chiral chromatography, fractional cyrstallization of diastereomeric salts and the like.

Compounds of this invention may be formulated into pharmaceutical compositions together with pharmaceutically acceptable carriers for oral administration in solid or liquid form, or for intraveneous, rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement of the active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

The general scheme for producing compounds useful in this invention is illustrated and explained on the following page.

General Scheme

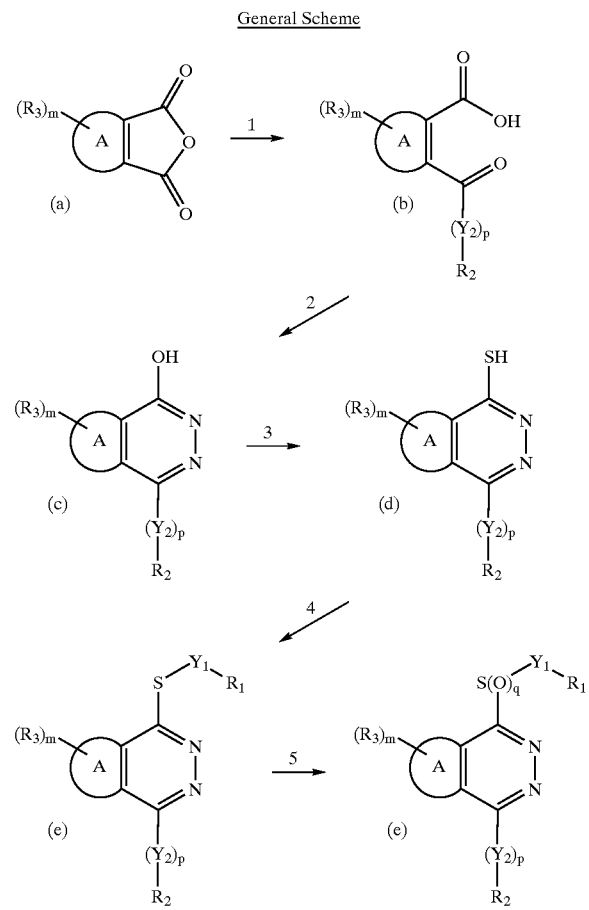

A γ-ketocarboxylic acid (b) can be obtained from a substituted or unsubstituted anhydride (a) (reaction 1) by a Friedel-Crafts reaction (OS, CV-I, 517, 1941) with a substituted or unsubstituted aromatic compound ($R_2$—H, method A) or by reaction with a Grignard reagent Hal-(Mg—$(Y_2)_p$—$R_2$), followed by acidic workup (method B).

Condensation of acid (b) with hydrazine leads to the annellated pyridazine derivative (c) (reaction 2). The hydroxy phthalazine (c) is converted to the thiophthalazine derivative (d) by stirring with Lawesson's reagent for 2 hours at (80–90° C.) (reaction 3). After treatment with base (e.g., KOH), a SN-reaction with a substituted alkyl or arylhalide generates the product (e)(reaction 4). Oxidation of (e) with oxone® gives the sulfone derivative (f) (reaction 5) where q=2.). Oxidation of (e) with $H_2O_2$ gives the sulfoxide derivative (g) (reaction 5) where q=1.

A number of γ-ketocarboxylic acids (b) are commercially available (e.g., from Aldrich Chemical Co.)

2-benzoylbenzoic acid
2[4-(dibutylamino)-2-hydroxybenzoyl]benzoic acid
3-benzoyl-2-pyridine carboxylic acid
2-(4-fluorobenzoyl)benzoic acid
2-aminobenzophenone-2'-carboxylic acid
2(3-amino-4-chlorobenzoyl)benzoic acid
4-[4-(2-carboxybenzoyl)phenyl]butyric acid
2-(4-chlorobenzoyl)benzoic acid In summary, the reagents and conditions for the general schemes are as follows:

(1)
  Method A: Friedel-Crafts Reaction $R_2$—H and $AlCl_3$ as a catalyst (p=0).
  Method B: Grignard Reaction Hal-Mg—$(Y_2)_p$—$R_2$, acid (p=0 or 1).
(2) $NH_2NH_2$
(3) Lawesson's reagent (Aldrich), toluene, 80–90° C.
(4)
  a) KOH
  b) Hal-$Y_1$—$R_1$
(5) Oxone® (Aldrich) DMA or $H_2O_2$ The foregoing may be better understood from the following examples that are presented for the purposes of illustration and are not intended to limit the scope of the invention. As used in the following examples, the references to substituents such as $R_1$ $Y_1$, A, etc. refer to the corresponding substituents in Formula I above.

EXAMPLE 1

1-Benzylthio-4-Phenylphthalazine

A. 1-Hydroxy-4-phenylphthalazine

The mixture of o-benzoyl benzoic acid (11.3 g; 0.05 mol) and hydrazine (0.15 mol) in ethanol (150 ml) is stirred at room temperature for 5–24 hours to give 1-hydroxy-4-phenyl phthalazine as a white precipitate which is filtered off and is washed with ethanol. (12.3 g)(m.p. 240° C.)

B. 4-Phenylphthalazine-1-thiol

1-Hydroxy-4-phenylphthalazine (0.31 g, 1.5 mmol) in toluene (30 ml) is allowed to react with Lawesson's reagent (0.6 g, 1.5 mmol) and the mixture is stirred in an oil bath. (80–90° C.) for 1.5 hour until all starting material is used up. Evaporation of the solvent gives a yellow solid which is stirred with isopropyl ether. Filtration gives the title compound as a yellow solid which is recrystallized from hexane/THF/toluene:7.5/2.5/2.0 (0.3 g)

C. 1-Benzylthio-4-phenylphthalazine

To a suspension of 4-phenylphthalazine-1-thiol (238 mg; 1 mmol) in ethanol (30 ml), aqueous KOH (1 molar, 1 ml) and N,N-dimethylacetamide (30 ml) are added. After 10 minutes, benzylchloride (126 mg, 1 mmol) is added, and the mixture is stirred at room temperature overnight. The solution is concentrated, and water (20 ml) is added to the residual to give a precipitate. Filtration gives a light yellow solid ($R_1$=phenyl, $R_2$=phenyl, A=benzene, $Y_1$=$CH_2$, m=0, n=1, p=0, q=0).

Formula: $C_{21}H_{16}N_2S$

Molecular Mass: 328.44 g/mol

Melting point: 92° C.

$^1$H-NMR [ppm] (DMSO-$d_6$): 4.82 (s,2,$CH_2$); 7.34 (m,3, ar); 7.56 (m,3,ar.); 7.74 (m,3,ar.); 7.83 (m,3,ar.); 8.02 (dd, 1,ar.); 8.18 (dd,1,ar.);

IR [$cm^{-1}$] (KBr): 3058 ar-H; 1567 C=N; 1381 S—$CH_2$.

EXAMPLE 2

1-(2-Propenylthio)-4-Phenylphthalazine

To a suspension of 4-phenylphthalazine-1-thiol (Example 1B) (238 mg, 1 mmol) in ethanol (40 ml) is added aqueous KOH (1 molar, 1 ml). After 10 minutes, allylbromide (0.1 ml, 1 mmol) is added, and the mixture is stirred at room temperature for 4 days. After the solvent is evaporated, the residue is extracted with $CH_2Cl_2$. The organic phase is evaporated and the residue is stirred with isopropyl ether. Filtration gives the pure title compound, which is recrystallized from ethanol (130 mg). ($R_1$=vinyl, $R_2$=phenyl, A=benzene, $Y_1$=$CH_2$, m=0, n=1, p=0, q=0).

Formula: $C_{17}H_{14}N_2S$

Molecular Mass: 278.38 g/mol

Melting point: 83° C.

$^1$H-NMR [ppm] (DMSO-$d_6$): 4.21 (d,2,$CH_2$); 5.22 (d,1, =CH); 5.42 (dd,1,=CH); 6.17 (dd,1,=CH); 7.55 (dd,3, ar.); 7.73 (d,2,ar.); 7.85 (m,3,ar.); 7.92 (d,2,ar.); 8.18 (d,1, ar.);

IR [$cm^{-1}$] (KBr): 3051 ar-H; 2921 $CH_2$; 1634 C=N; 1288 S—C.

EXAMPLE 3

1-Methylthio-4-Phenylphthalazine

The procedure described in Example 2 is followed with methyliodide (0.06 ml, 1 mmol) as the alkylating reagent instead of allylbromide to yield the title compound. ($R_1$=H, $R_2$=phenyl, A=benzene, $Y_1$=$CH_2$, m=0, n=1, p=0, q=0).

Formula: $C_{15}H_{12}N_2S$

Molecular Mass: 252.34 g/mol

Melting point: 147° C.

$^1$H-NMR [ppm] (DMSO-$d_6$): 2.87 (s,3,—$CH_3$); 7.54 (m,2,ar.); 7.73 (m,2,ar.); 7.84 (m,3,ar.); 8.02 (d,1,ar.); 8.21 (d,1,ar.);

IR [$cm^{31\ 1}$] (KBr): 3075 ar-H; 2977 $CH_3$; 1588 C=N; 1287 S—C.

EXAMPLE 4

1-(3-Chlorobenzylthio)-4-Phenylphthalazine

To a suspension of 4-phenylphthalazine-1-thiol (1 mmol; from Example 1B) in ethanol (20 ml) is added aqueous KOH (1 molar;1 ml), and the mixture is stirred for 10 minutes to give a clear solution. 3-Chlorobenzylbromide (0.13 ml, 1 mmol) is added at room temperature, and the solution is stirred overnight. Work-up yields the title compound as a white solid (40 mg).

($R_1$=3-chlorophenyl, $R_2$=phenyl, A=benzene, $Y_1$=$CH_2$, m=0, n=1, p=0, q=0)

Formula: $C_{21}H_{15}N_2ClS$

Molecular Mass: 362,87 g/mol

Melting point: 85° C.

$^1$H-NMR [ppm] ($CDCl_3$): 4.77 (s,2,$CH_2$); 7.24 (br,2,ar); 7.46 (m,1,ar); 7.56 (m,4,ar); 7.73(m,2,ar); 7.85 (m,3,ar); 8.03 (m,1,ar); 8.15 (m,1,ar);

IR [$cm^{-1}$] (KBr): 3050 ar-H; 1600 C=N; 1573 C=C; 1289 S—C;

EXAMPLE 5

1-(2-Chlorobenzylthio)-4-Phenylphthalazine

When 2-chlorobenzylbromide (0.13 ml; 1 mmol) is used in the procedure described in Example 4, instead of 3-chlorobenzyl bromide, 1-(2-chlorobenzylthio)-4-phenylphthalazine is obtained ($R_1$=2-chlorophenyl, $R_2$=phenyl, A=benzene, $Y_1$=$CH_2$, m=0, n=1, p=0, q=0).

EXAMPLE 6

1-(3,4-Difluorobenzylthio)-4-Phenylphthalazine

When 3,4-difluorobenzylbromide (0.13 ml; 1 mmol) is used in the procedure described in Example 4, instead of 3-chlorobenzyl bromide, 1-(3,4-difluorobenzylmercapto)-4-phenylphthalazine is obtained ($R_1$=3, 4-difluorophenyl, $R_2$=phenyl, A=benzene, $Y_1$=$CH_2$, m=0, n=1, p=0, q 0).

EXAMPLE 7

1-(3-Fluorobenzylthio)-4-Phenylphthalazine

When 3-fluorobenzylchroride (0.12 ml; 1 mmol) is used in the procedure described in Example 4 instead of 3-chlorobenzyl bromide, 2-(3-fluorobenzylthio)-4-phenylphthalazine is obtained ($R_1$=3-fluorophenyl, $R_2$=phenyl, A=benzene, $Y_1$=$CH_2$, m=0, n=1, p=0, q=0).

EXAMPLE 8

1-(3,5-Difluorobenzylthio)-4-Phenylphthalazine

When 3,5-difluorobenzylbromide (0.14 ml; 1 mmol) is used in the procedure described in Example 4 , instead of 3-chlorobenzyl bromide, 2-(3,5-difluorobenzylthio)-4-phenylphthalazine is obtained ($R_1$=3,5-difluorophenyl, $R_2$=phenyl, A=benzene, $Y_1$=$CH_2$, m=0, n=1, p=0, q=0).

EXAMPLE 9

1-(2,5-Difluorobenzylthio)-4-Phenylphthalazine

When 2,5-difluorobenzylbromide (0.14 ml; 1 mmol) is used in the procedure described in Example 4, instead of 3-chlorobenzyl bromide, 1-(2,5-difluorobenzylthio)-4-phenylphthalazine (0.29 g) is obtained ($R_1$=2,5-difluorophenyl, $R_2$=phenyl, A=benzene, $Y_1$=$CH_2$, m=0, n=1, p=0, q=0).

EXAMPLE 10

1-(4-Chlorobenzylthio)-4-Phenylphthalazine

When 4-chlorobenzylbromide (0.32 ml; 2 mmol) is used in the procedure described in Example 4, instead of 3-chlorobenzyl bromide, and the reaction is stirred overnight in an oil bath (55° C.), 1-(4-chlorobenzylthio)-4-phenylphthalazine is obtained ($R_1$=4-chlorophenyl, $R_2$=phenyl, A=benzene, $Y_1$=$CH_2$, m=0, n=1, p=0, q=0).

EXAMPLE 11

1-(4-Fluorobenzylthio)-4-Phenylphthalazine

When 4-fluorobenzylbromide (0.13 ml; 1 mmol) is used in the procedure described in Example 4 instead of 3-chlorobenzyl bromide, 1-(4-fluorobenzylthio)-4-phenylphthalazine is obtained as a white solid after stirring the reaction mixture for 2 days and purifying the white precipitate by column chromatography (hexane/isopropylether 5/5) ($R_1$=4-fluorophenyl, $R_2$=phenyl, A=benzene, $Y_1$=$CH_2$, m=0, n=1, p=0, q=0).

Formula: $C_{21}H_{15}N_2FS$

Molecular Mass: 346.42 g/mol

Melting point: 104° C.

$^1$H-NMR [ppm] ($CDCl_3$): 4.77 (s,2,$CH_2$); 7.01 (t,2,ar); 7.56 (m,5,ar); 7.73 (m,2,ar); 7.84 (m,2,ar); 8.02 (dd,1,ar); 8.16 (dd,1,ar);

IR [$cm^{-1}$] (KBr): 3053 ar-H; 1610 C=N; 1513 C=C; 1237 S—C.

EXAMPLE 12

1-(2,4-Difluorobenzylthio)-4-Phenylphthalazine

When 2,4-difluorobenzylchloride (0.13 ml; 1 mmol) is used in the procedure described in Example 4 instead of 3-chlorobenzyl bromide, 1-(2,4-difluorobenzylthio)-4-phenylphthalazine is obtained as a white solid ($R_1$=2,4-difluorophenyl, $R_2$=phenyl, A=benzene, $Y_1$=$CH_2$, m=0, n=1, p=0, q=0).

EXAMPLE 13

1-(2,3-Difluorobenzylthio)-4-Phenylphthalazine

When α-bromo-2,3-difluorotoluene (0.13 ml; 1.5 mmol) is used in the procedure described in Example 4, instead of 3-chlorobenzyl bromide, 1-(2,3-difluorobenzylthio)-4-phenylphthalazine is obtained as a white solid ($R_1$=2,3-difluorophenyl, $R_2$=phenyl, A=benzene, $Y_1$=$CH_2$, m=0, n=1, p=0, q=0).

EXAMPLE 14

1-(3,4-Methylenedioxybenzylthio)-4-Phenylphthalazine

When 3,4-methylenedioxy benzylbromide (80 mg; 0.37 mmol) is used in the procedure described in Example 4 instead of 3-chlorobenzyl bromide, 1-(3,4-methylenedioxybenzylthio)-4-phenylphthalazine is obtained as a white solid after stirring the mixture for two days at room temperature ($R_1$=3,4-methylendioxyphenyl, $R_2$=phenyl, A=benzene, $Y_1$=$CH_2$, m=0, n=1, p=0, q=0).

EXAMPLE 15

1-(2-Chloro-6-Fluorobenzylthio)-4-Phenylphthalazine

When 2-chloro-6-fluorobenzylchloride (0.13 ml, 1 mmol) is used in the procedure described in Example 4 instead of 3-chlorobenzyl bromide, 1-(2-chloro-6-fluorobenzylthio)4-phenylphthalazine is obtained after stirring the reaction mixture overnight in an oil bath (56° C.) ($R_1$=2-chloro-6-fluorophenyl, $R_2$=phenyl, A=benzene, $Y_1$=$CH_2$, m=0, n=1, p=0, q=0).

EXAMPLE 16

1-(2,6-Difluorobenzylthio)-4-Phenylphthalazine

When 2,6-difluorobenzyl bromide (0.21 g; 1 mmol) is used in the procedure described in Example 4 instead of 3-chlorobenzyl bromide, 1-(2,6-difluorobenzylthio)-4-phenylphthalazine is obtained after stirring the mixture 2 days at room temperature ($R_1$=2,6-difluorophenyl, $R_2$=phenyl, A=benzene, $Y_1$=$CH_2$, m=0, n=1, p=0, q=0).

EXAMPLE 17

1-(2-Propargylthio)-4-Phenylphthalazine

When propargyl bromide (0.11 ml, 1 mmol) is used in the general procedure described in Example 4 instead of 3-chlorobenzyl bromide, 1-(2-propargylthio)-4-phenylphthalazine is obtained as a white solid after stirring the mixture for 2 hours and filtering it ($R_1$=ethinyl, $R_2$=phenyl, A=benzene, $Y_1$=$CH_2$, n=1, m=0, p=0, q=0).

Formula: $C_{17}H_{12}N_2S$

Molecular Mass: 276.35 g/mol

Melting point: 111° C.

$^1$H-NMR [ppm] ($CDCl_3$): 2.26 (br,1,alkyne); 4.35 (d,2,$CH_2$); 7.55 (dd,3,ar); 7.73 (m,2,ar); 7.87 (m,2,ar); 8.05 (dd,1,ar); 8.13 (d,1,ar);

IR [cm$^{-1}$] (KBr): 3272 alkyne; 3060 ar-H; 2920 $CH_2$; 1570 C=N; 1244 S—C.

EXAMPLE 18

1-(Benzylsulfonyl)-4-Phenylphthalazine

1-Benzylthio-4-phenylphthalazine (98 mg; 0.3 mmol from Example 1B) in N,N-dimethylacetamide (13 ml) is cooled in an ice bath. Oxone® (2$KHSO_5$·$KHSO_4$·$K_2SO_4$) (670 mg; 1.1 mmol) is added, followed by the stepwise addition of water (1.4 ml). The mixture is stirred at room temperature for 2 days, is poured into ice water, is stirred 10 minutes and is filtered to give the title compound as a solid (53 mg) ($R_1$=phenyl, $R_2$=phenyl, A=benzene, $Y_1$=$CH_2$, m=0, n=1, p=0, q=2).

Formula: $C_{19}H_{16}N_2O_2S$

Molecular Mass: 360.43 g/mol

Melting Point: 235° C.

$^1$H-NMR [ppm] ($CDCl_3$): 7.53 (m, 5, ar); 7.58 (m, 3, ar); 7.80 (m, 5, ar), 8.54 (t,1,ar); 10.25 (br,2,$CH_2$)

IR [cm$^{-1}$] (KBr): 3060 ar-H; 2900 $CH_2$; 1676 S=O; 1587 C=N.

EXAMPLE 19

Methyl-2-(4-Phenylthiophthalazinyl)acetate

A suspension of 4-phenylphthalazinethiol (0.23 g; 1 mmol from Example 1B) in ethanol (25 ml) is allowed to react with aqueous KOH (1N, 1 ml) and is stirred at room temperature. After 5 minutes, methylbromoacetate (1.1 ml, 1 mmol) is added to the clear solution, which is allowed to react overnight until no starting material remains (TLC-control). Water (10 ml) is added to the solution. Filtration of the white precipitate gives a mixture that contains two compounds. Flash chromatography (hexane/isopropylether: 4/6) yields the title compound ($R_1$=$CH_3$, $R_2$=phenyl, A=benzene, $Y_1$=$CH_2$—$CO_2$, m=0, n=1, p=0, q=0).

Formula: $C_{17}H_{14}N_2O_2S$

Molecular Mass: 310.37 g/mol

Melting point: 132° C.

$^1$H-NMR [ppm] ($CDCl_3$): 3.80 (s,3,$CH_3$); 4.39 (s,2,$CH_2$); 7.54 (dd,3,ar); 7.71 (dd,2,ar); 7.87 (m,2,ar); 8.03 (dd,1,ar); 8.19 (d,1,ar);

IR [cm$^{-1}$] (KBr): 3050 ar-H; 2952, 2931 C—H; 1732 C=O; 1580 C=N; 1168 S—C.

EXAMPLE 20

1-(2'-Naphthylmethylthio)-4-Phenylphthalazine

Aqueous potassium hydroxide (1 N, 1 mmol) is added to the suspension of 4-phenylphthalazine-1-thiol (0.23 g, 1 mmol from Example 1B) in ethanol (20 ml). After 5 minutes, 2-bromomethylnaphthalene (0.22 g, 1 mmol) is added to the mixture which is stirred at room temperature overnight. Water (10 ml) is added to the solution. Filtration gives the title compound as white crystals (0.35 g) ($R_1$=2-naphthyl, $R_2$=phenyl, A=benzene, $Y_1$=$CH_2$, m=0, n=1, p=0, q=0).

Formula: $C_{25}H_{18}N_2S$

Molecular Mass: 378.49 g/mol

Melting point: 160° C.

$^1$H-NMR [ppm] ($CDCl_3$): 4.98 (s,2,$CH_2$); 7.47 (t,2,ar); 7.56 (dd,3,ar); 7.69 (m,1,ar); 7.74 (m,2,ar); 7.83 (m,5,ar); 8.03 (m,2,ar); 8.16 (m,1,ar);

IR [cm$^{-1}$] (KBr): 3050 ar-H; 1594 C=N; 1570 C=C; 1280 S—C.

EXAMPLE 21

1-(t-Butyl 2'Mercaptoacetate)-4-Phenylphthalazine

Aqueous potassium hydroxide (1 N, 1 mmol) is added to the suspension of 4-phenylphthalazinethiol (0.23 g, 1 mmol from Example 1B) in ethanol (25 ml). After 15 minutes, the resulting clear solution is charged with t-butylbromoacetate and is stirred at room temperature overnight. Water (10 ml) is added to dissolve the KBr. Precipitation of the title compound occurs at −10° C. Filtration yields the title compound as white crystals (0.22 g) ($R_1$=t-butyl, $R_2$=phenyl, A=benzene, $Y_1$=$CH_2$—$CO_2$, m=0, n=1, p=0, q=0).

Formula: $C_{20}H_{20}N_2O_2S$

Molecular Mass: 352.45 g/mol

Melting Point: 116° C.

$^1$H-NMR [ppm] ($CDCl_3$): 1.49 (s,9,t-butyl); 4.30 (s, 2, $CH_2$); 7.54 (m,3,ar); 7.70 (m,2,ar); 7.86 (m, 2, ar); 8:01 (d, 1, ar); 8.20 (d, 1, ar);

IR [cm$^{-1}$] (KBr): 3070 ar-H; 1726 C=O; 1311 S—C.

EXAMPLE 22

1-(3-Chlorobenzylthio)-4-(2-Pyridyl)-Phthalazine

A. 1-Hydroxy-4-(2-Pyridyl)phthalazine

A Grignard solution of 2-bromomagnesium pyridine (4.55 g, 25 mmol) in ether is added to phthalic anhydride (7.4 g, 50 mmol). The reaction gas mixture is stirred under reflux for 2 hours, cooled with ice and is then hydrolysed with HCl to yield crude 2-(2-pyridylcarbonyl)benzoic acid hydrochloride as residue after evaporation. Excess phtalic acid is removed by trifuration with diethyl ether.

A 3M-solution of hydrazine (20 ml, 60 mmol) in ethanol is added to the solution of crude 2-(2-pyridylcarbonyl) benzoic acid hydrochloride(4.54 g, 20 mmol), and the mixture is stirred at room temperature for 5 hours. Precipitation yields 1-hydroxy-4-(2-pyridyl)phthalazine.

B. 4-(2-Pyridyl)phthalazine-1-thiol

The product from part A of this example is subjected to the general procedure of Example 1, part B to give 4-(2-pyridyl)phthalazine-1-thiol.

C. 1-(3-Chlorobenzylthio)-4-(2-pyridyl)-phthalazine

The product from part B of this example is subjected to the general procedure of Example 1, part C with 3-chlorobenzyl bromide as the alkylating reagent to yield 1-(3-chlorobenzylthio)-4-(2-pyridyl)phthalazine ($R_1$=3-chlorophenyl, $R_2$=2-pyridyl, A=benzene, $Y_1$=$CH_2$, m=0, n=1, p=0, q=0).

EXAMPLE 23

1-(3-Chlorobenzylthio)-4-(5-Pyrimidinyl) Phthalazine

The general procedure described in Example 22, part A is followed with phthalic anhydride and 5-bromomagnesium pyrimidine in ether to yield 1-hydroxy-4-(pyrimidin-5-yl)-phthalazine. The general procedures of parts B–C in Example 22 are followed to produce the title compound, 1-(3-chlorobenzylthio)-4-(5-pyrimidinyl)phthalazine ($R_1$= 3-chlorophenyl, $R_2$=pyrimidin-5-yl, A=benzene, $Y_1$=$CH_2$, m=0, n=1, p=0, q=0)

EXAMPLE 24

1-(3-Chlorobenzylthio)-4-(3-Pyridinyl)Phthalazine

The general procedure described in Example 23, part A is followed with phthalic anhydride and 3-bromomagnesium pyridine in ether to yield 1-hydroxy-4-(3-pyridyl) phthalazine. The general procedures of parts B–C in Example 22 are followed to produce the title compound, 1-(3-chlorobenzylthio)-4-(3-pyridinyl)phthalazine ($R_1$=3-chlorophenyl, $R_2$=pyridin-3-yl, A=benzene, $Y_1$=$CH_2$, m=0, n=1, p=0, q=0).

EXAMPLE 25

1-(2-Pyridinylmercapto)-4-(2-Thiophenyl) Phthalazine

The general procedure described in Example 22, part A is followed with phthalic anhydride and 2-bromomagnesium thiophene in ether to yield 1-hydroxy-4-(thiophen-2-yl) phthalazine. The general procedures of parts B–C in Example 22 are followed to produce the title compound, 1-(2-pyridinylmercapto)-4-(2-thiophenyl)-phthalazine ($R_1$= pyridin-2-yl, $R_2$=thiophen-2-yl, A=benzene, $Y_1$=$CH_2$, m=0, n=0, p=0, q=0).

EXAMPLE 26

1-(2-Thiophenylmethylmercapto)-4-(5-Pyrimidinl) Phthalazine

The procedure described in Example 22, part A is followed with phthalic anhydride and 5-bromomagnesium pyrimidine in ether to yield 1-hydroxy-4-(pyrimidin-5-yl) phthalazine. The general procedures of parts B–C in Example 22 are followed substituting 3-chlorobenzyl bromide with 2-bromomethylthiophene, to obtain the title compound, 1-(2-thiophenylmethylmercapto)-4-(5-pyrimidinyl)-phthalazine ($R_1$=thiophen-2-yl, $R_2$=pyrimidin-5-yl, A=benzene, $Y_1$=$CH_2$, m=0, n=1, p=0, q=0).

EXAMPLE 27

1-(3-Chlorobenzylthio)-4-Phenyl-5-Azaphthalazine

A. 4-Phenyl-1,2-dihydro-5-azaphthalazin-1-ol

A 3M ethanolic solution of hydrazine (20 ml, 60 mmol) is added to an ethanolic solution of 2-benzoyl-3-pyridine carboxylic acid (Aldrich product) (4.54 g, 20 mmol), and the mixture is stirred at room temperature for 24 hours. Precipitation yields 4-Phenyl-1,2-dihydro-5-azaphthalazin-1-ol.

B. 1-(3-Chlorobenzylthio)-4-phenyl-5-azphthalazine

The general procedures described in Example 22, parts B and C are followed with 4-phenyl-1,2-dihydro-5-azaphthalazin-1-ol as the starting material to obtain the title compound ($R_1$=3-chlorophenyl, $R_2$=phenyl, A=2,3 fused pyridine, $Y_1$=$CH_2$, m=0, n=1, p=0, q=0).

EXAMPLE 28

1-(2-Thiophenmethylmercapto)-4-Phenyl-5-Azanhthalazine 4-phenyl-1,2-dihydro-5-azaphthalazin-1-ol (Example 28, part A) is subjected to the general procedure described in Example 22, parts B and C with 2-bromomethylthiophene as the alkylating reagent to yield 1-(2-thiophenmethylmercapto)-4-phenyl-5-azaphthalazine ($R_1$= thiophen-2-yl, $R_2$=phenyl, A=2,3 fused pyridine ring, $Y_1$=$CH_2$, m=0, n=1, p=0, q=0).

EXAMPLE 29

1-(2-Pyridinmercapto)-4-(4-Chlorophenyl)-Phthalazine

A. 4-(4-Chlorobenzyl)-1-hydroxy-phthalazine.

A 3 M ethanolic solution of hydrazine (20 ml, 60 mmol) is added to 2-(4-chlorobenzoyl)benzoic acid (5.5 g, 20 mmol), and the mixture is stirred at room temperature for 5 hours. Precipitation gives 4-(4-chlorophenyl)-1-hydroxy-phthalazine.

B. 1-(2-Pyridinmercapto)-4-(4-chlorophenyl)-phthalazine.

The product of the previous reaction (A) is subjected to the general procedures of Example 22, parts B and C with 2-bromopyridine as the alkylating reagent to yield 1-(2-pyridimnercapto)-4-(4-chlorophenyl)-1-phthalazine ($R_1$=2-pyridinyl, $R_2$=4-chlorophenyl, A=benzene, m=0, n=0, p=0, q=0).

EXAMPLE 30

1-(2-Pyridylmethylthio)-4-(4-Pyridylmethyl)-Phthalazine

A. 3-(4-Pyridylmethylene)-isobenzofuran-1-one

In accordance with the procedure described in Lombardino, J.O.C. Vol. 32, pp. 1988–1992 (1967), a solution of isobenzofuran-1-one (13.4 g, 0.1 mol) and 4-pyridine carboxaldehyde (10.7 g, 0.1 mol) in 100 ml dry methanol are refluxed for 2 hours. The solvent is evaporated, and the product, 3-(4-pyridylmethylene)-isobenzofuran-1-one, is used in the next step without further purification.

B. 4-(4-Pyridylmethyl)-1-phthalazinol

The general procedure described in Example 29, part A is followed with 3-(4-pyridylmethylene)-isobenzofuran-1-one instead of 2-(4-chlorobenzyl carbonyl) benzoic acid as the starting material to yield 4-(4-pyridylmethyl)-1-phthalazinol.

C. 1-(2-Pyridylmethylthio)-4-(4-pyridyhmethyl)-Phthalazine

The product of the previous reaction (B) is subjected to the general procedures of Example 22, parts B and C with 2-bromomethylpyridine as the alkylating reagent to yield 1-(2-pyridylmethylthio)-4-(4-pyridylmethyl)-phthalazine ($R_1$=2-pyridyl, $R_2$=4-pyridyl, $Y_1$=$CH_2$, $Y_2$=$CH_2$, A=benzene, m=0, n=1, p=1, q=0).

EXAMPLE 31

1-(2-Thiophenmethylthio)-4-(3-Pyridylmethyl)-Phthalazine

A. 3-(3-Pyridylmethylene)isobenzofuran-1-one

Following the procedure described in Example 30, part A, the 3-pyridine carboxaldehyde is used instead of the 4-pyridine carboxaldehyde to give the title compound.

B. 4-(3-Pyridylmethyl)-1-Phthalazinol

To produce the title compound, the procedure described in Example 30, part B is followed with 3-(3-pyridylmethylene) isobenzofuran-1-one instead of 3-(4-pyridylmethylene) isobenzofuran-1-one as the starting material.

C. 1-(2-Thiophenylmethylthio)-4-(3-pyridylmethyl)-phthalazine.

The product of the previous reaction (B) is subjected to the general procedures of Example 22, parts B and C with 2-bromomethylthiophene as the alkylating reagent to yield the title compound ($R_1$=2-thiophenyl, $R_2$=3-pyridyl, A=benzene, $Y_1$=$CH_2$, m=0, n=1, p=1, q=0, $Y_2$=$CH_2$).

EXAMPLE 32

1-(2-Pyridylmethylthio)-4-(2-Pyridylmethyl)-Phthalazine

A. 3-(2-Pyridyhnethylene)isobenzofuran-1-one

With the general procedure described in Example 30, part A, 2-pyridine carboxaldehyde is used instead of 4-pyridine carboxaldehyde to give 3-(2-pyridylmethylene)-isobenzofuran-1-one.

B. 4-(2-Pyridylmethyl)-1-phthalazinol

With the procedure described in Example 30, part B, 3-(2-pyridylmethylene)isobenzofuran-1-one is used as the starting material instead of 3-(4-pyridylmethylene) isobenzofuran-1-one to give the title compound.

C. 1-(2-Pyridylmethylthio)-4-(2-pyridylmethyl)-phthalazine 4-(2-Pyridylmethyl)-1-phthalazinol is subjected to the general procedures of Example 22, parts B and C with 2-bromomethylpyridine as the alkylating reagent to yield 1-(2-pyridylmethyl-thio)-4-(2-pyridylmethyl)-1-phthalazine ($R_1$=2-pyridyl, $R_2$=2-pyridyl, A=benzene, $Y_1$=$CH_2$, m=0, n=1, p=1, $Y_2$=$CH_2$, q=0).

EXAMPLE 33

1-(3-Chlorobenzylthio)-4-Benzyl-Phthalazine

4-Benzyl-1-phthalazinone is synthesized according to Chem. Pharm. Bull 39, pp. 2009–2015 (1991). It is then subjected to the general procedure Example 1, parts B and C with 3-chlorobenzyl bromide as the alkylating reagent to yield the title compound ($R_1$=3-chlorophenyl, $R_2$=phenyl, A=benzene, $Y_1$=$CH_2$, m=0, n=1, p=1, $Y_2$=$CH_2$, q=0).

EXAMPLE 34

1-(3-Chlorobenzylthio)-5,8-Difluoro-4-(2-Pyridyl)Phthalazine

A. 5,8-Difluoro-4-(2-pyridyl)phthalazin-1-ol

A Grignard solution of 2-bromomagnesium pyridine (25 mmol) in ether is added to 3,6-difluorophthalic anhydride (50 mmol). The reaction mixture is stirred under reflux for 2 hours, cooled with ice and is then hydrolysed with HCl gas to yield crude 3,6-difluoro-2-(2-pyridylcarbonyl)benzoic acid hydrochloride.

A 3M-solution of hydrazine (60 mmol) in ethanol is added to a solution of crude 3,6-difluoro-2-(2-pyridylcarbonyl) benzoic acid hydrochloride (20 mmol), and the mixture is stirred at room temperature for 5 hours. Precipitation yields 5,8-difluoro-4-(2-pyridyl)-1-phthalazinol.

B. 1-(3-Chlorobenzylthio)-5,8-difluoro-4-(pyridin-2-yl)phthalazine

The product from part B of this Example is subjected to the general procedures of Example 23, parts B and C with 3-chlorobenzyl bromide as the alkylating reagent to yield 1-(3-chlorobenzylthio)-5,8-difluoro-4-(2-pyridyl) phthalazine ($R_1$=3-chlorophenyl, $R_2$=2-pyridyl, A=benzene, n=1, p=0, $R_3$=5,8-difluoro, m=2, $Y_2$=$CH_2$, q=0).

EXAMPLE 35

1-Ethylthio-4-Phenylphthalazine

The procedure described in Example 2 is followed with ethyl iodide (0.08 ml, 1 mmol) as the alkylating agent instead of alkyl bromide to yield the title compound 1-ethylthio-4-phenylphthalazine ($R_1$=$CH_3$, $R_2$=phenyl, A=benzene, $Y_1$=$CH_2$, n=1, p=0, m=0, q=0).

Formula: $C_{16}H_{14}N_2S$

Molecular Mass: 266.36 g/mol

Melting point: 93° C.

$^1$H-NMR [ppm] (DMSO-$d_6$): 1.54 (t,3,—$CH_3$); 3.54 (q,2, $CH_2$); 7.54 (m,2,ar.); 7.75 (m,2,ar.); 7.84 (m,3,ar.); 8.02 (d,1,ar.); 8.21 (d,1,ar.);

IR [cm$^{-1}$] (KBr): 3060 ar-H; 2950 $CH_2$,$CH_3$; 1625 C=N; 1286 S—C.

Biological Effects (A) Growth Inhibition

The compounds of this invention were assayed for their growth inhibitory activity on the human colon carcinoma cell line, SW-480 obtained from ATCC (Rockville, Md.), to ascertain the degree of growth inhibition (Skehan et al., J. Natl. Cancer Instit. 82:1107–1112, 1990). Growth inhibition of this cell line is indicative of a benefit on precancerous lesions and neoplasms. The cell line and growth assay employed for such experiments are well characterized, and are used to evaluate the anti-neoplastic properties of compounds (Piazza, Cancer Research Vol. 57, pp. 2452–2459, 1997). The assay is used by the United States National Cancer Institute in its screening program for new anti-cancer drugs.

Drug stock solutions were made in 100% DMSO and were then diluted with RPMI media for cell culture testing. All drug solutions were prepared fresh on the day of testing. The cultured cells were obtained at passage #99 and grown in RPMI media supplemented with 5% fetal calf serum, and 2 mM glutamine, 100 $\mu$/ml penicillin, 100 U/ml streptomycin, and 0.25 $\mu$g/ml amphotericin. The cultures were maintained in a humidified atmosphere of 95% air and 5% $CO_2$ at 37° C. The cultures were passaged at preconfluent densities using a solution of 0.05% trypsin and 0.53 mM EDTA. Cells were plated at 1000 cells/well for 96 well flat-bottom microtiter plates.

Tumor cell growth inhibition was assessed using the Sulforhodamine B (SRB) protein binding assay. In this assay, tumor cells were plated in 96-well plates and treated with drug-containing media for six days (continuous exposure). For each plate, 6 wells were designated as no treatment controls, six wells as vehicle (0.1% DMSO) controls, and the remaining wells for drug dilutions with three wells per drug concentration. At the end of the exposure period, the cells were fixed and stained with sulforhodamine B, a protein binding dye. The dye was then solubilized, and the optical density of the resulting solution was determined on a 96-well plate reader. The mean optical density of the treated wells was then divided by the mean optical density in the control wells (6 wells of each) to determine the effect of the drug on the cells. Dye intensity is proportional to the number of cells or amount of protein per well. The resultant "percent inhibition" values, which then represents the degree of growth inhibition, for the indicated compounds from the Examples are tabulated in Table 1.

TABLE 1

| EXAMPLE | % Growth Inhibition at 100 $\mu$M |
|---|---|
| 1 | 85% |
| 2 | 87% |
| 3 | <50% |
| 4 | 81% |
| 11 | 76% |
| 19 | 61% |
| 20 | <50% |
| 21 | 51% |
| 22 | 88% |
| 36 | 89% |

For one compound of this invention, an $IC_{50}$ value was determined. An $IC_{50}$ value is equivalent to the concentration of compound needed to inhibit tumor cell growth by 50%. The $IC_{50}$ value was obtained graphically by plotting and connecting the mean growth inhibition values for each drug concentration tested. The experiment included three wells per drug concentration. Concentration was plotted on a log scale on the X-axis. The $IC_{50}$ value obtained for the compound of Example 36 is shown in Table 1.

TABLE 2

| EXAMPLE | $IC_{50}$ ($\mu$M) |
|---|---|
| 36 | 32 |

(B) Cyclooxygenase (COX I) Inhibition

COX I catalyzes the formation of prostaglandins and thromboxane by the oxidative metabolism of arachidonic acid. Compounds of this invention, as well as a positive control, (sulindac sulfide) were evaluated to determine whether they inhibited purified cyclooxygenase Type 1 (see Table 3 below).

The COX I was purified from ram seminal vesicles, as described by Boopathy, R. and Balasubramanian, J. 239:371–377, 1988. COX I activity was assayed as described by Evans, A. T. et al., "Actions of Cannabis Constituents on Enzymes Of Arachidonate Metabolism Anti-Inflammatory Potential," Biochem. Pharmacol., 36:2035–2037, 1987. Purified COX I was incubated with arachidonic acid (100 $\mu$M) for 2.0 min at 37° C. in the presence or absence of test compounds. The assay was terminated by the addition of TCA, and COX I activity was determined by absorbance at 530 mn.

TABLE 3

| EXAMPLE | COX I<br>% Inhibition (100 $\mu$M) |
|---|---|
| Sulindac sulfide | 97% |
| 1 | 30% |
| 2 | 62% |
| 3 | 73% |
| 4 | <25% |
| 11 | <25% |
| 18 | 81% |
| 19 | <25% |
| 20 | <25% |
| 22 | <25% |
| 36 | <25% |

As explained above, the compounds of this invention can be formulated with pharmaceutically acceptable carriers into unit dosage forms in a conventional manner so that the patient in need of therapy for precancerous lesions can periodically (e.g., once or more times per day) take a compound according to the methods of this invention. The exact initial dose of the compounds of this invention can be determined with reasonable experimentation. One skilled in the art should understand that the initial dosage should be sufficient to achieve a blood plasma concentration approaching a percentage of the $IC_{50}$ value of the compound, with the percentage depending on the chemopreventative or chemotherapeutic indication. The initial dosage calculation would also take into consideration several factors, such as the formulation and mode of administration, e.g. oral or intravenous, of the particular compound. For example, assuming a patient with an average circulatory system volume of about four liters, based on the $IC_{50}$ value above for compounds of this invention, one would calculate a dosage of about 34 mg of such compounds for intravenous administration to achieve a systemic circulatory concentration equivalent to the $IC_{50}$ concentration.

We claim:
1. A compound of the formula:

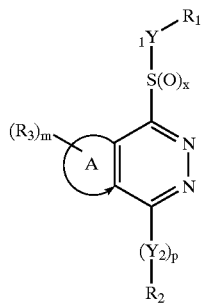

wherein
$Y_1$ and $Y_2$ are independently selected from the group of $(CH_2)_n$, —C(X)—NH—, —$(CH_2)_n$—C(X)—O—, and X is O or S;

$R_1$ is selected from the group consisting of lower alkyl, lower alkenyl, lower alkynyl, hydrogen, and substituted or unsubstituted phenyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, morpholinyl, naphthyl, tetrazolyl, triazinyl, furfuryl and thiophenyl, wherein said substituents are one to three independently selected from the group consisting of halogen, lower alkyl, lower alkoxy, amino, lower alkylamino, di-lower alkylamino, hydroxy, nitro, cyano, carboxyl, lower alkyl mercapto, and lower alkyl sulfonyl;

$R_2$ is selected from the group consisting of substituted or unsubstituted phenyl, benzyl, pyrrolyl, pyrrolidinyl, pyrazolyl, pyrazolidinyl, imidazolidinyl, piperidinyl, pyrazinyl, piperazinyl, pyrimidinyl, tetrazolyl, morpholinyl, triazinyl, furfuryl and thiophenyl, wherein said substituents are one to three independently selected from the group consisting of halogen, lower alkyl, lower alkoxy, amino, lower alkylamino, di-lower alkylamino, hydroxy, nitro, cyano, carboxyl, aminosulfonyl, lower alkyl mercapto, and lower alkyl;

A is a pyridine ring fused with the pyridazine ring;

$R_3$ is independently selected in each instance form the group consisting of halogen, lower alkyl, lower alkoxy, amino, lower alkylamino, di-lower alkylamino, hydroxy, nitro, cyano, carboxyl, lower alkyl mercapto, and lower alkyl sulfonyl;

m is an integer from 0 to 4;
n is an integer from 0 to 3
p is 0 or 1; x is 0 to 2; and
pharmaceutically acceptable salts thereof.

2. A compound of claim 1 wherein $R_1$ is selected from the group consisting of hydrogen, lower alkyl, lower alkenyl, lower alkynyl, and substituted or unsubstituted phenyl, pyridinyl, pyrrolyl, naphtyl, pyrazolyl, imidazolyl, pyrazinyl, pyrimidinyl, morpholinyl, triazinyl, furfuryl and thiophenyl, wherein said substituents are one or two independently selected from the group consisting of halogen, lower alkoxy, di-lower alkylamino, hydroxy, cyano, carboxyl, lower alkyl mercapto, and lower alkyl sulfonyl.

3. A compound of claim 2 wherein $R_1$ is selected from the group consisting of hydrogen and substituted or unsubstituted phenyl, pyridinyl, pyrazinyl, pyrimidinyl, triazinyl, naphthyl, furfuryl and thiophenyl, wherein said substituent is one member selected from the group consisting of halogen, lower alkoxy, di-lower alkylamino, cyano, and lower alkyl sulfonyl.

4. A compound of claim 1 wherein $R_2$ is selected from the group consisting of substituted or unsubstituted phenyl, benzyl, pyrrolyl, pyrazolyl, pyrazinyl, pyrimidinyl, morpholinyl, triazinyl, furfuryl and thiophenyl, wherein said substituents are one or two independently selected from the group consisting of halogen, lower alkyl, lower alkoxy, di-lower alkylamino, hydroxy, carboxyl, aminosulfonyl, lower alkyl mercapto, and lower alkyl.

5. A compound of claim 4 wherein $R_2$ is selected from the group consisting of substituted or unsubstituted phenyl, benzyl, pyrazinyl, pyrimidinyl, triazinyl, furfuryl and thiophenyl, wherein said substituent is one member selected from the group consisting of halogen, lower alkyl, lower alkoxy, di-lower alkylamino, aminosulfonyl, and lower alkyl mercapto.

6. A method of treating a patient having neoplasia comprising administering a pharmacologically effective amount of a compound of Formula I to the patient with a neoplasia sensitive to such a compound:

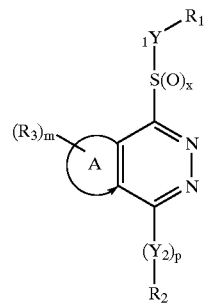

wherein
$Y_1$ and $Y_2$ are independently selected from the group consisting of $(CH_2)_n$, —C(X)—NH—, —$(CH_2)_n$—C(X)—O—, and X is O or S;

$R_1$ is selected from the group consisting of lower alkyl, lower alkenyl, lower alkynyl, hydrogen and substituted or unsubstituted phenyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, morpholinyl, naphthyl, tetrazolyl, triazinyl, furfuryl and thiophenyl, wherein said substituents are one to three independently selected from the group consisting of halogen, lower alkyl, lower alkoxy, amino, lower alkylamino, di-lower alkylamino, hydroxy, nitro, cyano, carboxyl, lower alkyl mercapto, and lower alkyl sulfonyl;

$R_2$ is selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, tetrazolyl, morpholinyl, triazinyl, furfuryl and thiophenyl, wherein said substituents are one to three independently selected from the group consisting of halogen, lower alkyl, lower alkoxy, amino, lower alkylamino, di-lower alkylamino, hydroxy, nitro, cyano, carboxyl, aminosulfonyl, lower alkyl mercapto, and lower alkyl;

"A" is a pyridine ring fused with the pyridazine ring;

$R_3$ is independently selected in each instance form the group consisting of halogen, lower alkyl, lower alkoxy, amino, lower alkylamino, di-lower alkylamino, hydroxy, nitro, cyano, carboxyl, lower alkyl mercapto, and lower alkyl sulfonyl;

m is an integer from 0 to 4;

n is an integer from 0 to 3;

p is 0 or 1;

x is an integer from 0 to 2; and pharmaceutically acceptable salts thereof.

7. A method of claim 4 wherein n is an integer from 0 to 2.

8. A compound of claim 1 wherein p is 0 or 1.

9. A compound of claim 7 wherein p is 0.

10. A compound of claim 1 wherein $R_3$ is independently selected in each instance from the group consisting of halogen, lower alkyl, lower alkoxy, di-lower alkylamino, hydroxy, carboxyl, sulfonylamido, lower alkyl mercapto, and lower alkyl sulfonyl; and m is an integer from 0 to 2.

11. A compound of claim 10 wherein $R_3$ is independently selected in each instance from the group consisting of halogen, lower alkyl, lower alkoxy, di-lower alkylamino, and lower alkyl mercapto; and m is 0 or 1.

12. A compound of claim 1 wherein n is an integer from 0 to 2.

13. A compound of claim 11 wherein n is 0 or 1.

14. A pharmaceutical composition comprising a pharmaceutically acceptable carrier and a compound of the formula:

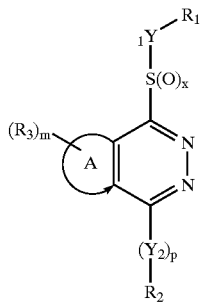

wherein $Y_1$ and $Y_2$ are independently selected from the group consisting of $(CH_2)_n$, —C(X)—NH—, —$(CH_2)_n$—C(X)—O—, and X is O or S;

$R_1$ is selected from the group consisting of lower alkyl, lower alkenyl, lower alkynyl, hydrogen and substituted or unsubstituted phenyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, morpholinyl, naphthyl, tetrazolyl, triazinyl, furfuryl and thiophenyl, wherein said substituents are one to three independently selected from the group consisting of halogen, lower alkyl, lower alkoxy, amino, lower alkylamnino, di-lower alkyl amino, hydroxy, nitro, cyano, carboxyl, lower alkyl mercapto, and lower alkyl sulfonyl;

$R_2$ is selected from the group consisting of substituted or unsubstituted phenyl, benzyl, pyrrolyl, pyrrolidinyl, pyrazolyl, pyrazolidinyl, imidazolyl, imidazolidinyl, piperidinyl, pyrazinyl, piperazinyl, pyrimidinyl, tetrazolyl, morpholinyl, triazinyl, furfuryl and thiophenyl, wherein said substituents are one to three independently selected from the group consisting of halogen, lower alkyl, lower alkoxy, amino, lower alkylamino, di-lower alkylamino, hydroxy, nitro, cyano, carboxyl, aminosulfonyl, lower alkyl mercapto, and lower alkyl;

"A" is a pyridine ring fused with the pyridazine ring;

$R_3$ is independently selected in each instance form the group consisting of halogen, lower alkyl, lower alkoxy, amino, lower alkylamnino, di-lower alkylamino, hydroxy, nitro, cyano, carboxyl, lower alkyl mercapto, and lower alkyl sulfonyl;

m is an integer from 0 to 4;

n is an integer from 0 to 3 p is 0 or 1;

x is an integer from 0 to 2; and pharmaceutically acceptable salts thereof.

15. A pharmaceutical composition of claim 14 wherein $R_1$ is selected from the group consisting of hydrogen, lower alkyl, lower alkenyl, lower alkynyl, and substituted or unsubstituted phenyl, pyridinyl, pyrrolyl, pyrazolyl, imidazolyl, pyrazinyl, pyrimidinyl, morpholinyl, triazinyl, furfuryl and thiophenyl, wherein said substituents are one or two independently selected from the group consisting of halogen, lower alkoxy, di-lower alkylamino, hydroxy, cyano, carboxyl, lower alkyl mercapto, and lower alkyl sulfonyl.

16. A pharmaceutical composition of claim 15 where in $R_1$ is selected from the group consisting of hydrogen and substituted or unsubstituted phenyl, pyridinyl, pyrazinyl, pyrimidinyl, triazinyl, naphthyl, furfuryl and thiophenyl, wherein said substituent is one member selected from the group consisting of halogen, lower alkoxy, di-lower alkylamino, cyano, and lower alkyl sulfonyl.

17. A pharmaceutical composition of claim 14 wherein $R_2$ is selected from the group consisting of substituted or unsubstituted phenyl, benzyl, pyrrolyl, pyrazolyl, pyrazinyl, pyrimidinyl, morpholinyl, triazinyl, furfuryl and thiophenyl, wherein said substituents are one or two independently selected from the group consisting of halogen, lower alkyl, lower alkoxy, di-lower alkylamino, hydroxy, carboxyl, aminosulfonyl, lower alkyl mercapto, and lower alkyl.

18. A pharmaceutical composition of claim 17 wherein $R_2$ is selected from the group consisting of substituted or unsubstituted phenyl, benzyl, pyrazinyl, pyrimidinyl, triazinyl, furfuryl and thiophenyl, wherein said substituent is one member selected from the group consisting of halogen, lower alkyl, lower alkoxy, di-lower alkylamino, aminosulfonyl, and lower alkyl mercapto.

19. A method of claim 7 wherein n is 0 or 1.

20. A method of claim 4 wherein $R_3$ is independently selected in each instance from the group consisting of halogen, lower alkyl, lower alkoxy, di-lower alkylamino, hydroxy, carboxyl, sulfonylamido, lower alkyl mercapto, and lower alkyl sulfonyl; and m is an integer from 0 to 2.

21. A pharmaceutical composition of claim 14 wherein p is 0 or 1.

22. A pharmaceutical composition of claim 21 wherein p is 0.

23. A pharmaceutical composition of claim 14 wherein $R_3$ is independently selected in each instance from the group consisting of halogen, lower alkyl, lower alkoxy, di-lower alkylamino, hydroxy, carboxyl, sulfonylamido, lower alkyl mercapto, and lower alkyl sulfonyl; and m is an integer from 0 to 2.

24. A pharmaceutical composition of claim 23 wherein $R_3$ is independently selected in each instance from the group consisting of halogen, lower alkyl lower alkoxy, di-lower alkylarino, and lower alkyl mercapto; and m is 0 or 1.

25. A pharmaceutical composition of claim 14 wherein n is an integer from 0 to 2.

26. A compound of claim 25 wherein n is 0 or 1.

27. A method of claim 20 wherein $R_3$ is independently selected in each instance from the group consisting of halogen, lower alkyl, lower alkoxy, di-lower alkylamino, and lower alkyl mercapto; and m is 0 or 1.

28. A method of claim 27 wherein $R_1$ is selected from the group consisting of hydrogen, lower alkyl, lower alkenyl, lower alkynyl, and substituted or unsubstituted phenyl, pyridinyl, pyrrolyl, naphthyl, pyrazolyl, imidazolyl, pyrazinyl, pyrimidinyl, morpholinyl, triazinyl, furfuryl and thiophenyl, wherein said substituents are one or two independently selected from the group consisting of halogen, lower alkoxy, di-lower alkylamino, hydroxy, cyano, carboxyl, lower alkyl mercapto, and lower alkyl sulfonyl.

29. A method of claim 28 wherein $R_1$ is selected from the group consisting of hydrogen and substituted or unsubstituted phenyl, pyridinyl, pyrazinyl, pyrimidinyl, triazinyl, napthyl, furfuryl and thiophenyl, wherein said substituent is one member selected from the group consisting of halogen, lower alkoxy, di-lower alkylamino, cyano, and lower alkyl sulfonyl.

30. A method of claim 27 wherein $R_2$ is selected from the group consisting of substituted or unsubstituted phenyl, benzyl, pyridinyl, pyrrolyl, pyrazolyl, imidazolyl, pyrazinyl, pyrimidinyl, morpholinyl, triazinyl, furfuryl and thiophenyl, wherein said substituents are one or two independently selected from the group consisting of halogen, lower alkyl, lower alkoxy, di-lower alkylamino, hydroxy, carboxyl, aminosulfonyl, lower alkyl mercapto, and lower alkyl.

31. A method of claim 30 wherein $R_2$ is selected from the group consisting of substituted or unsubstituted phenyl, benzyl, pyridinyl, pyrazinyl, pyrimidinyl, triazinyl, furfuryl and thiophenyl, wherein said substituent is one member selected from the group consisting of halogen, lower alkyl, lower alkoxy, di-lower alkylamino, aminosulfonyl, and lower alkyl mercapto.

32. A method of claim 6 wherein p is 0 or 1.

33. A method of claim 32 wherein p is 0.

* * * * *